United States Patent
Oka et al.

(10) Patent No.: US 7,176,464 B2
(45) Date of Patent: Feb. 13, 2007

(54) METHOD OF AND APPARATUS FOR DETERMINING THE AMOUNT OF IMPURITY IN GAS

(75) Inventors: Koichi Oka, Otsu (JP); Satoshi Nitta, Kameoka (JP)

(73) Assignee: Otsuka Electronics Co., Ltd., Osaka (JP)

( * ) Notice: Subject to any disclaimer, the term of this patent is extended or adjusted under 35 U.S.C. 154(b) by 18 days.

(21) Appl. No.: 11/181,777

(22) Filed: Jul. 15, 2005

(65) Prior Publication Data

US 2006/0011844 A1   Jan. 19, 2006

(30) Foreign Application Priority Data

Jul. 16, 2004   (JP) .............................. 2004-210693

(51) Int. Cl.
*G01J 5/02*   (2006.01)
(52) U.S. Cl. .................................... 250/343
(58) Field of Classification Search ................ 250/343
See application file for complete search history.

(56) References Cited

U.S. PATENT DOCUMENTS

| | | | | |
|---|---|---|---|---|
| 6,040,915 A | * | 3/2000 | Wu et al. | .................... 356/435 |
| 6,636,316 B1 | * | 10/2003 | Matsumoto et al. | ........ 356/437 |
| 2002/0061594 A1 | | 5/2002 | Itou et al. | |

FOREIGN PATENT DOCUMENTS

| | | |
|---|---|---|
| GB | 2 054 843 A | 2/1981 |
| JP | 2001-228085 | 8/2001 |
| WO | WO 00/42427 | 7/2000 |
| WO | WO 2004/027410 A1 | 4/2004 |

* cited by examiner

*Primary Examiner*—David Porta
*Assistant Examiner*—Marcus Taningco
(74) *Attorney, Agent, or Firm*—Finnegan, Henderson, Farabow, Garrett, & Dunner, L.L.P.

(57) ABSTRACT

Impurity is removed from gas, the resultant gas is introduced into a cell 15, and the intensity of light transmitted through the cell 15 is measured as a reference. Gas containing impurity of which concentration is known, is introduced into the cell 15, and the intensity of light transmitted through the cell 15 is measured with the temperature and pressure maintained at those used at the measurement of the reference light intensity. Then, the absorbance of the impurity is obtained according to the ratio of the two light intensity data obtained by the two measurements above-mentioned. The impurity absorbance thus obtained is stored, in a memory 20$a$, as a function of an impurity concentration. Gas containing impurity of which concentration is unknown, is introduced into the cell 15, and the intensity of light transmitted through the cell 15 is measured with the temperature and pressure maintained at those used at the measurements above-mentioned. The absorbance of the impurity is obtained according to the last-measured light intensity and the reference light intensity. The absorbance thus obtained is applied to the function, thereby to obtain the impurity concentration.

6 Claims, 6 Drawing Sheets

METHOD OF AND APPARATUS FOR DETERMINING THE AMOUNT OF IMPURITY IN GAS

BACKGROUND OF THE INVENTION

1. Field of the Invention

The present invention relates to method of and apparatus for determining the amount of impurity mixed in gas.

2. Description of Related Art

In a conventional method of determining the amount of impurity in gas with the use of an infrared spectrometer, when measuring the concentration of a trace impurity gas, the infrared absorption peak of the main component gas overlaps the infrared absorption peak of the trace gas component, causing the measurement of the trace impurity gas to be very difficult.

The following description will discuss, by way of example, a measurement of a trace moisture contained, as impurity gas, in ammonia gas.

There has conventionally been proposed a method of measuring such a trace moisture at a wavenumber at which the infrared absorption of ammonia and the infrared absorption of the moisture do not overlap each other (Japanese Patent Laid-Open Publication No. 2001-228085).

However, even by this method of measurement at a wavenumber at which the infrared absorption of ammonia and the infrared absorption of the moisture do not overlap each other, when the concentration of impurity gas is very small, the infrared absorption spectrum of the impurity gas overlaps the infrared absorption spectrum of ammonia. This makes the measurement of the concentration of the impurity gas makes difficult.

In view of the foregoing, it is an object of the present invention to provide method of and apparatus for determining the amount of impurity in gas, capable of accurately measuring the concentration of the impurity gas even though the impurity gas concentration is very small.

SUMMARY OF THE INVENTION

According to the present invention, a method of determining the concentration of impurity mixed in gas, comprises the steps of: removing impurity from gas, introducing the gas into a first cell, and measuring the intensity of light transmitted through the first cell; introducing gas containing impurity of which concentration is known, into the first cell or a second cell having an optical path length equal to that of the first cell, and measuring the intensity of light transmitted through the first cell or the second cell with the temperature and pressure maintained at those used at the measurement above-mentioned; obtaining the absorbance of the impurity based on the ratio of the two light intensity data obtained by the two measurements above-mentioned, and storing this impurity absorbance in terms of a function of an impurity concentration; introducing gas containing impurity of which concentration is unknown, into the first cell, the second cell or a third cell having an optical path length equal to that of the first cell, and measuring the intensity of light transmitted through the first cell, the second cell or the third cell with the temperature and pressure maintained at those used at the measurements above-mentioned; and obtaining the absorbance of the impurity based on the light intensity just obtained and the intensity of the light transmitted through the first cell, and applying the thus obtained absorbance to the function, thereby to obtain the impurity concentration.

According to the method above-mentioned, the intensity of light which has absorbed a sample gas with its impurity gas removed, is measured as a reference, and there is also measured, under conditions of the same temperature, the same pressure and the same optical path length, the intensity of light which has absorbed a sample gas containing impurity gas of which concentration is known. Then, the ratio (the difference for a logarithm) between these two light intensity data, is calculated to obtain the absorbance of the impurity, and the impurity absorbance thus obtained is stored in terms of a function of an impurity concentration. Then, there is measured, under conditions of the same temperature, the same pressure and the same optical path length, the intensity of light which has absorbed a sample gas containing impurity gas of which concentration is unknown. The impurity absorbance is then obtained. When the impurity absorbance thus obtained is applied to the function, the impurity concentration can be obtained.

Accordingly, there can accurately be measured the concentration of the impurity alone with the influence of the sample gas removed.

The present invention also provides apparatus for determining the concentration of impurity mixed in gas, comprising: a cell into which gas is introduced; a light source for irradiating light to the cell; a detector for measuring the intensity of light transmitted through the cell; heat-insulating means for maintaining the cell at a fixed temperature; pressure adjusting means for adjusting the pressure of the gas in the cell to a predetermined value; a first gas introducing system for introducing, into the cell, a sample gas of which impurity concentration is to be measured; a second gas introducing system for introducing, into the cell, gas containing impurity of which concentration is known; an impurity removing device disposed in the first gas introducing system for removing impurity from a sample gas; first light intensity measuring means for introducing, into the cell, gas of which impurity has been removed by the impurity removing device, and for measuring the intensity of light transmitted through the cell; second light intensity measuring means for introducing, into the cell, gas containing impurity of which concentration is known, and for measuring the intensity of light transmitted through the cell; storing means for dividing the light intensity obtained by the measurement conducted with the second light intensity measuring means, by the light intensity obtained by the measurement conducted with the first light intensity measuring means, thereby to obtain the absorbance of the impurity, and for storing the impurity absorbance thus obtained in terms of a function of an impurity concentration; third light intensity measuring means for introducing, into the cell, gas containing impurity of which concentration is unknown, and for measuring the intensity of light transmitted through the cell; and concentration measuring means for dividing the light intensity obtained by the measurement conducted with the third light intensity measuring means, by the light intensity obtained by the measurement conducted with the first light intensity measuring means, thereby to obtain the absorbance of the impurity, and for applying the thus obtained impurity absorbance to the function stored in the storing means, thereby to obtain the impurity concentration.

This apparatus for determining the concentration of impurity mixed in gas, is in accordance with an invention identical with the invention for the method of determining the concentration of impurity mixed in gas. With this apparatus, there can accurately be measured the concentration of the impurity alone with the influence of the sample gas removed.

Preferably, the light source and the detector are separately housed in respective airtight containers. According to the arrangement above-mentioned, the airtight containers can readily be evacuated and filled with gas which does not absorb light at the wavelength of the absorption spectrum of the impurity. This prevents the light source and the detector from being contaminated. Accordingly, the impurity spectrum to be measured is not affected by contamination, thus preventing a measuring error from occurring.

It is preferable that the joint portion between the first airtight container and the cell is capable of maintaining the airtightness in the first airtight container with the cell removed, and that the joint portion between the second airtight container and the cell is capable of maintaining the airtightness in the second airtight container with the cell removed. According to the arrangement above-mentioned, the cell can readily be replaced with other cell with the airtightness of each of the airtight containers maintained.

Preferably, a power source unit for supplying an electric power to the light source or the detector, is disposed outside of the first and second airtight containers. Such an arrangement prevents the effect of radiation from the power source unit serving as a heat generating source, from being lowered.

It is preferable that there is also disposed a computer for achieving the function of each of the first light intensity measuring means, the second light intensity measuring means, the storing means, the third light intensity measuring means and the concentration measuring means, and that the computer is disposed outside of the first and second airtight containers. Such an arrangement too prevents the effect of radiation from the computer from being lowered, likewise in the power source unit.

The foregoing and other advantages, characteristics and effects of the present invention will become more apparent from the following detailed description of the preferred embodiments with reference to the attached drawings.

DESCRIPTION OF THE PREFERRED EMBODIMENTS

Figure 1:
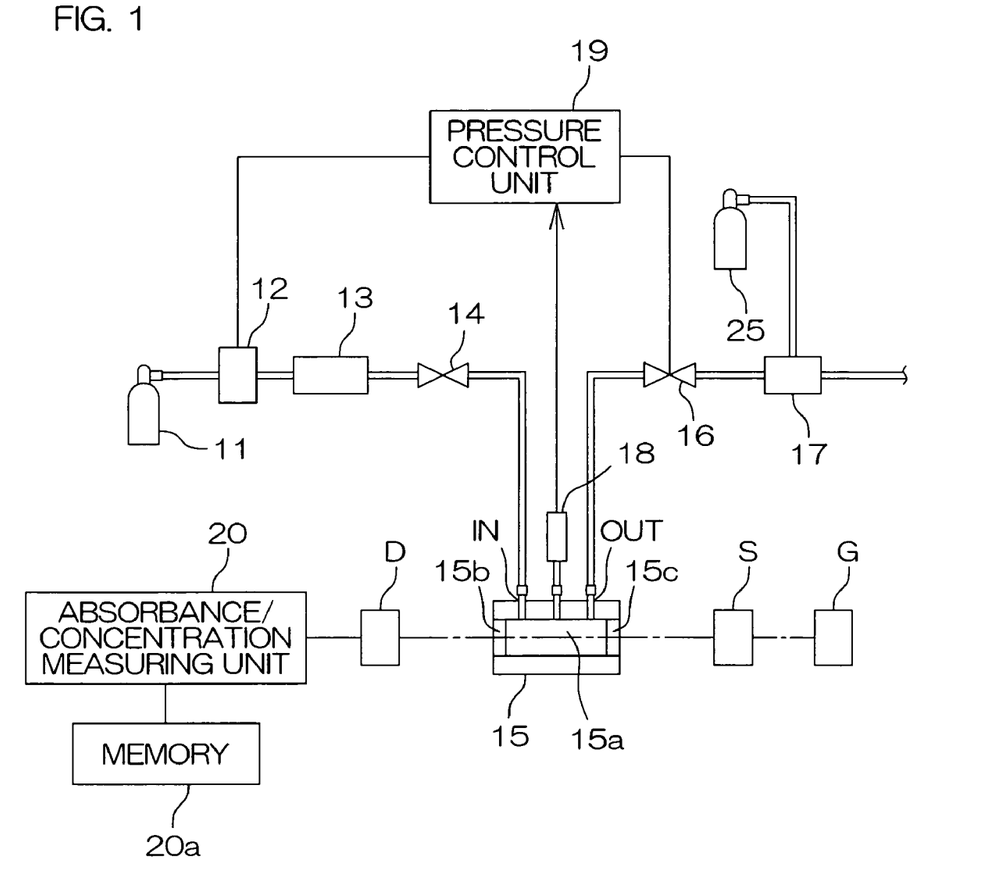
FIG. 1 is a view illustrating a measuring system for measuring the light intensity of a sample gas (reference) with impurity removed therefrom.

FIG. 1 is a view illustrating a measuring system for measuring the light intensity of a sample gas (reference) with impurity removed therefrom.

In FIG. 1, a sample bomb 11 containing a sample gas is connected to a gas inlet IN of a gas cell 15 through a mass flow controller 12 for adjusting the flow amount of gas, an impurity refining device 13 for removing impurity and an openable valve 14. This passage is referred to as a first gas introducing system.

On the other hand, an adjusting valve 16 and a vacuum generator 17 (which may also be a pressure ejector) for generating a negative pressure, are connected to a gas outlet OUT of the gas cell 15. The vacuum generator 17 is connected to a high-pressure gas bomb 25 containing air or nitrogen. With this construction, a pressure control of 0.1 Pa is possible in respect of atmosphere pressure (100 KPa).

In the present embodiment, the gas cell 15 serves as the first, the second and the third cell of the same optical path length as described in the SUMMARY OF THE INVENTION.

As shown in FIG. 1, the gas cell 15 has a case-like cell-chamber 15a having a fixed volume and light transmitting windows 15b, 15c respectively disposed at both end faces of the cell chamber 15a. The cell chamber 15a has the gas inlet IN and the gas outlet OUT, and further has a port to which connected is a pressure transducer 18 for measuring the pressure in the cell chamber 15a.

The mass flow controller 12, the adjusting valve 16 and the pressure transducer 18 are connected to a pressure control unit 19. The pressure control unit 19 is arranged to adjust, based on the pressure value measured by the pressure transducer 18, the flow amount of a sample gas and the opening degree of the adjusting valve 16, thus maintaining the pressure in the gas cell 15 at a predetermined pressure.

The light transmitting windows 15b, 15c are for example sapphire transmitting windows which transmit infrared rays.

In order to keep the gas cell 15 at a predetermined temperature as much as possible, the gas cell 15 is surrounded by an insulating material such as expanded styrol or the like (not shown). The whole gas cell 15 is housed in a heat-insulating container (not shown) together with an infrared source G, a spectroscope or interferometer S and an infrared detector D, as will be discussed later. The inside of the heat-insulating container is maintained at a predetermined temperature by a heater, a Peltier element or the like.

The code G shows the infrared source G. Any optional infrared generating mode may be used. For example, a ceramics heater (surface temperature of 450° C.) or the like may be used. There is also disposed the spectroscope or interferometer S for selecting the wavelength of the infrared rays. There may also be disposed a chopper (not shown) for interrupting and passing, at regular cycles, light generated by the infrared source G.

Light irradiated from the infrared source G and entered into the gas cell 15 through the light transmitting window 15c, is emitted from the gas cell 15 through the light transmitting window 15b and then detected by the infrared detector D. The infrared detector D is formed by a DtGs detector (a deuterium triglycine sulfate detector), an InAs detector, a CCD element or the like.

A detection signal of the infrared detector D is analyzed by an absorbance/concentration measuring unit 20. The analyzing method will be discussed later.

The pressure control unit 19 and the absorbance/concentration measuring unit 20 are formed by a personal computer. Each of the processing functions of the pressure control unit 19 and the absorbance/concentration measuring unit 20, is achieved by the computer which executes a program stored in a predetermined medium such as a CD-ROM, a hard disk or the like. A memory 20a connected to the absorbance/concentration measuring unit 20, is realized by a writable configuration file prepared in a recording medium such as a hard disk or the like.

In the measuring system above-mentioned, impurity (e.g., moisture) in a sample gas (e.g., ammonia gas) stored in the sample bomb 11, is removed by an impurity absorbent (e.g., moisture absorbing chemicals such as a silica gel or the like) in the impurity refining device 13, and the sample gas is then guided into the gas cell 15.

The pressure in the gas cell 15 is measured by the pressure transducer 18. The pressure control unit 19 controls the mass flow controller 12 and the adjusting valve 16 such that the measured pressure value becomes a target value. By this feedback control, the inside of the gas cell 15 is finally maintained at the desired fixed pressure, which is referred to as Ps.

In this state, light is irradiated from the infrared source G to spectrally scan the spectroscope or interferometer S, and the intensity of the light transmitted through the gas cell 15 is read by the infrared detector D. Thus, there can be measured the light intensity spectrum of the sample gas with its impurity removed therefrom, the sample gas being filled in the gas cell 15. For example, when the sample gas is ammonia gas and the impurity is moisture, there can be obtained the light intensity spectrum of the ammonia gas with the moisture removed therefrom.

The obtained light intensity spectrum of the sample gas with the impurity removed therefrom, is useful for correcting the light amount variation of the infrared source G, the sensitivity variation of the detector, and the like.

Figure 2:
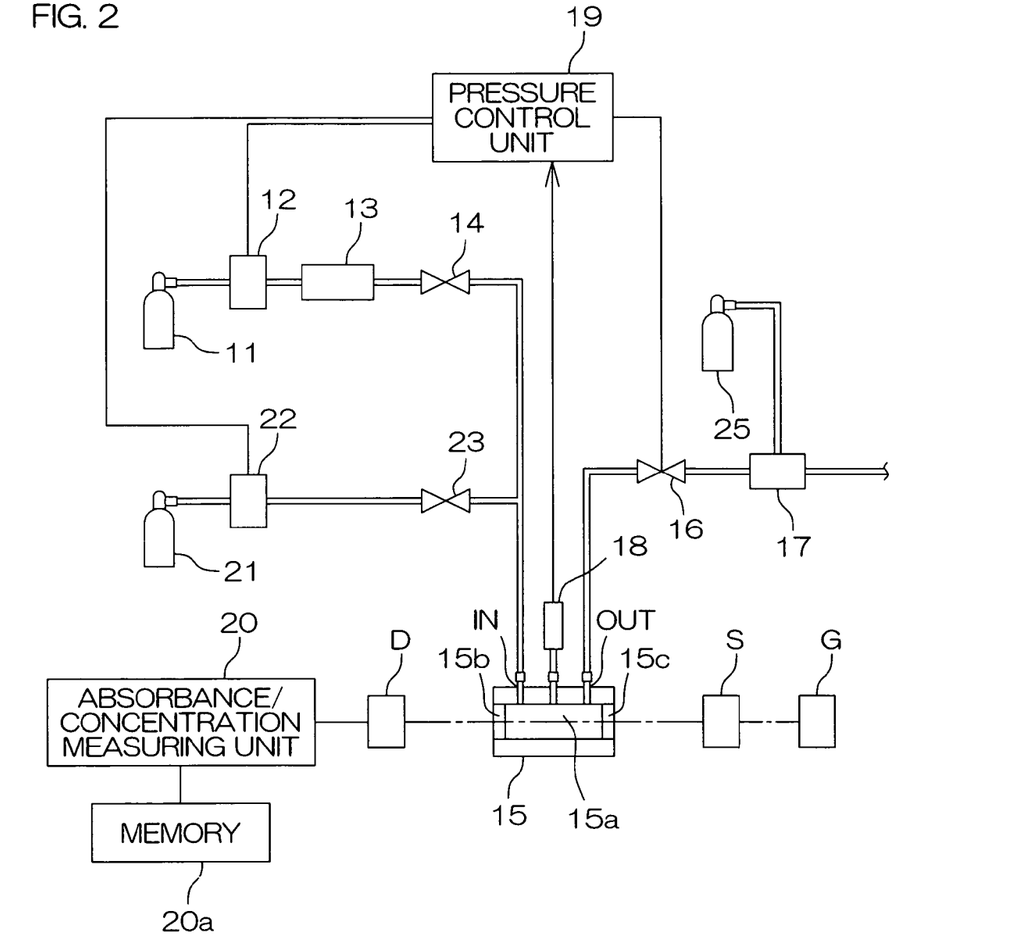
FIG. 2 is a view illustrating a measuring system for measuring, in order to prepare a calibration curve, a standard sample gas containing impurity of which concentration is known.

FIG. 2 is a view illustrating a measuring system for measuring, in order to prepare a calibration curve, a standard sample gas containing impurity of which concentration is known.

The measuring system in FIG. 2 is the same as that in FIG. 1 as to a system for supplying a sample gas from a sample bomb 11, a system for discharging the gas from a gas cell 15, and an optical measuring system for measuring a spectrum.

The measuring system in FIG. 2 is different from that in FIG. 1 in that there are disposed (i) a system including an impurity bomb 21 containing impurity gas of which concentration is known, (ii) a mass flow controller 22 and (iii) a valve 23 such that the impurity gas can be introduced into the gas cell 15. This passage is referred to as a second gas introducing system.

In the measuring system having the arrangement above-mentioned, the sample gas (e.g., ammonia gas) stored in the sample bomb 11 is introduced into the gas cell 15 through an impurity refining device 13 while the flow amount of the sample gas is controlled by a mass flow controller 12. The temperature of the gas cell 15 is equal to the temperature at which measurement was conducted with the measuring system in FIG. 1. At the same time, the impurity gas (e.g., steam) of which concentration is known, is introduced from the impurity bomb 21 into the gas cell 15 while its flow amount is controlled by the mass flow controller 22.

By adjusting the ratio between the flow amounts of the two mass flow controllers 12, 22, the partial pressure ratio r between the impurity gas and the sample gas can be optionally set. The impurity gas partial pressure to be set, is defined as Pi, while the sample gas pressure is defined as Ps. Pi is equal to rPs.

A pressure control unit 19 controls the mass flow controllers 12, 22 and an adjusting valve 16 such that the total pressure of the sample gas and the impurity gas is equal to (Pi+Ps).

It is noted that Pi is generally much smaller than Ps by 3 or 4 digits. Accordingly, it is practical that with Pi substantially disregarded, the pressure control unit 19 controls such that the total pressure of the sample gas and the impurity gas is not equal to (Pi+Ps), but is equal to Ps.

As discussed in the foregoing, there are present, in the gas cell 15, the sample gas at the partial pressure Ps and the impurity gas at the partial pressure Pi.

In this state, light is irradiated from an infrared source G to spectrally scan a spectroscope or interferometer S, and the intensity of the light transmitted through the gas cell 15 is read by an infrared detector D. Thus, there can be measured the absorption spectrum of the sample gas containing the impurity of which concentration is known, the sample gas being filled in the gas cell 15.

For example, when the sample gas is ammonia gas and the impurity is moisture, there can be obtained the absorption spectrum of the ammonia gas containing the moisture of which concentration is known.

Figure 3:
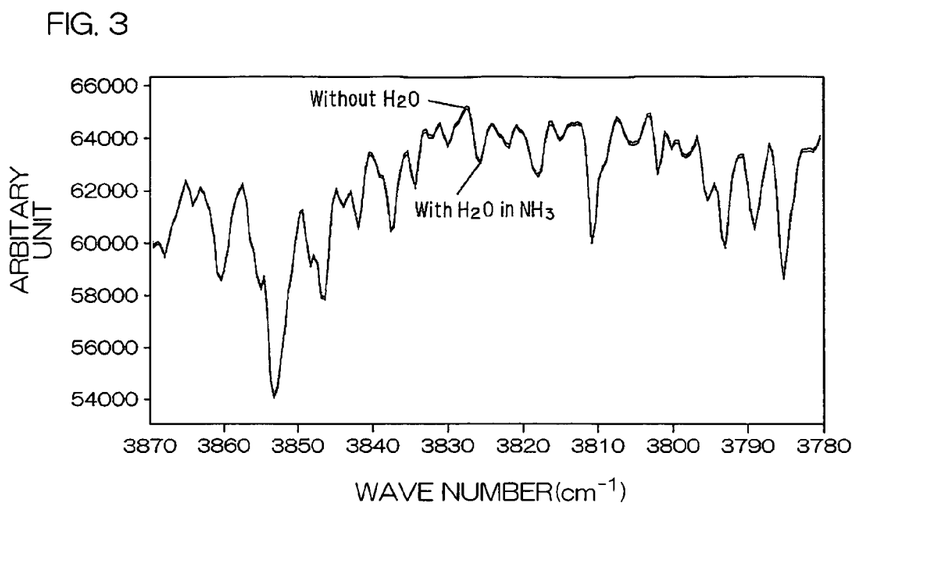
FIG. 3 is a graph comparably showing (i) the absorption spectrum of refined ammonia gas measured with the measuring system in FIG. 1, after the partial pressure ratio of impurity or steam has been adjusted such that the steam concentration is 100 ppb with respect to the ammonia gas, and (ii) the absorption spectrum of ammonia gas containing impurity or moisture, as measured with the measuring system in FIG. 2.

FIG. 3 is a graph comparably showing (i) the absorption spectrum of refined ammonia gas measured by the measuring system in FIG. 1, after the partial pressure ratio of impurity or steam has been adjusted such that the steam concentration is 100 ppb with respect to the ammonia gas, and (ii) the absorption spectrum of ammonia gas containing impurity or moisture, as measured by the measuring system in FIG. 2. In FIG. 3, the axis of abscissa shows a wavenumber ($cm^{-1}$), while the axis of ordinate is an arbitrary scale representing light intensity. The wavenumber on the axis of abscissa is in the range from 3870 ($cm^{-1}$) to 3780 ($cm^{-1}$), which is converted into the wavelength in the range from 2583 nm to 2645 nm.

FIG. 3 shows a difference, even very small, between the absorption spectrum of the refined ammonia gas and the absorption spectrum of the moisture-containing ammonia gas.

Figure 4:
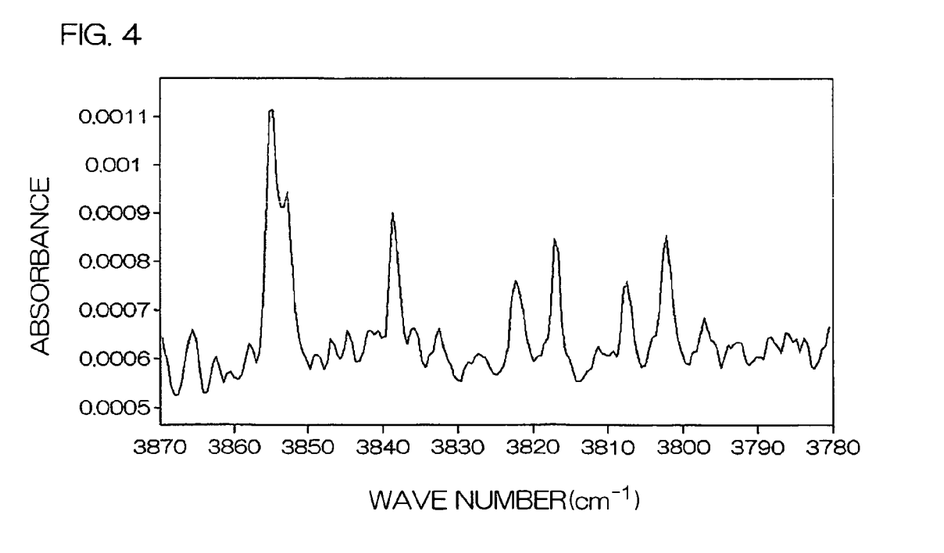
FIG. 4 is a graph showing the absorbance obtained based on the ratio of both absorption spectra in FIG. 3.

FIG. 4 is a graph showing the absorbance obtained by converting the ratio of both absorption spectra in FIG. 3. In FIG. 4, the axis of ordinate represents absorbance.

Here, the absorbance refers to a logarithm log (R0/R1) of the ratio (R0/R1) between a detected light intensity R0 obtained from measurement conducted with a sample gas free from impurity put in the gas cell 15, and a detected light intensity R1 obtained from measurement conducted with an impurity-containing sample gas put in the gas cell 15.

The graph in FIG. 4 shows the absorbance spectra of moisture having a concentration of 100 ppb, in the gas cell 15.

The absorbance/concentration measuring unit 20 stores, into the memory 20a, the spectra in FIG. 4 as data with respect to the wavelength.

Then, a great number of such data are obtained while changing the impurity concentration. For each wavelength, there is obtained a curve representing the relationship between the impurity concentration and the absorbance. This curve is referred to as a calibration curve.

It is presumed that the calibration curve inclination is not changed so much even though the wavelength is changed. Accordingly, there can be used the calibration curve for at least one representative wavelength. The representative wavelength refers to the wavelength at which the impurity spectrum shows a typical peak. For example, in FIG. 4, the highest peak appears at 3854 (cm$^{-1}$). Accordingly, the calibration curve at this wavelength may be used.

Figure 5:
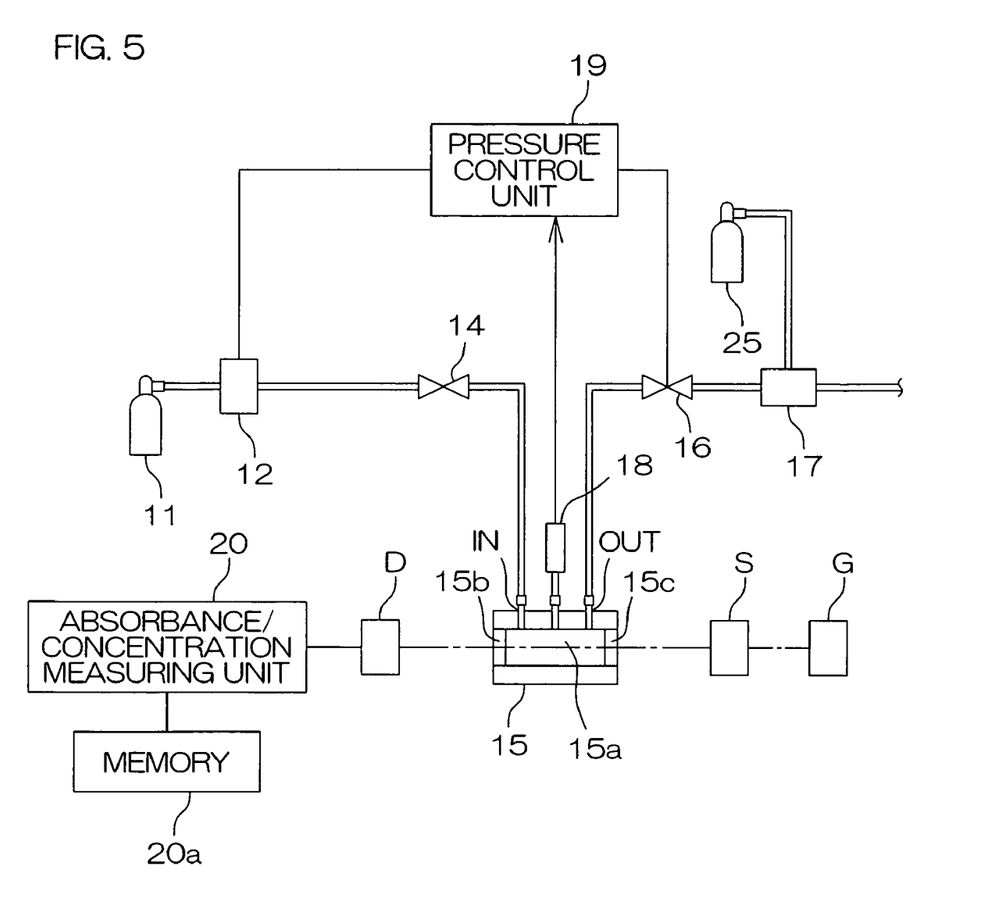
FIG. 5 is a view illustrating a measuring system for measuring a sample containing impurity of which concentration is unknown.

FIG. 5 is a view illustrating a measuring system for measuring a sample containing impurity of which concentration is unknown. The measuring system in FIG. 5 is basically the same as that in FIG. 1, except that there is not disposed an impurity refining device for removing impurity from sample gas. Accordingly, an impurity-containing sample gas is introduced into the gas cell 15 through the gas inlet IN. Here, the impurity concentration is unknown. Provision is made such that the temperature of the gas cell 15 at the time of measurement is the same as that of measurement conducted with each of the measuring systems in FIGS. 1 and 2. Provision is also made such that the pressure in the gas cell 15 is equal to the Ps mentioned earlier. The intensity spectrum measured with the measuring system in FIG. 5 is the intensity spectrum of a mixed gas of the sample gas and the impurity gas.

In the method of determining the amount of impurity in gas according to the present invention, the absorbance/concentration measuring unit 20 executes the following data processing.

First, the intensity spectrum measured by the measuring system in FIG. 5 is divided by the intensity spectrum measured by the measuring system in FIG. 1. Then, the absorbance spectrum inherent in the impurity gas can be obtained.

Then, the absorbance spectrum of the impurity gas is applied to the calibration curve already prepared, thereby to obtain the concentration of the impurity gas.

As stated above, the concentration of the impurity gas of which concentration is unknown, can be obtained.

The following will discuss modifications of the measuring system. In each of the measuring systems shown in FIGS. 1, 2 and 5, the infrared source G, the spectroscope or interferometer S and the infrared detector D are disposed in the air in the room. However, there are instances where there is to be measured a component, such as moisture, a carbon dioxide gas, a nitrogen oxide or the like, which absorbs infrared rays. However, such a component is contained in the air. Accordingly, it is required for a precise measurement to exclude such a component contained in the air, from the infrared source G, the spectroscope or interferometer S and the infrared detector D.

In this connection, it is considered that the infrared source G, the spectroscope or interferometer S, the infrared detector D and the like are disposed inside of a highly airtight container, and this container is evacuated or filled with highly pure gas which does not absorb infrared rays.

Figure 6:
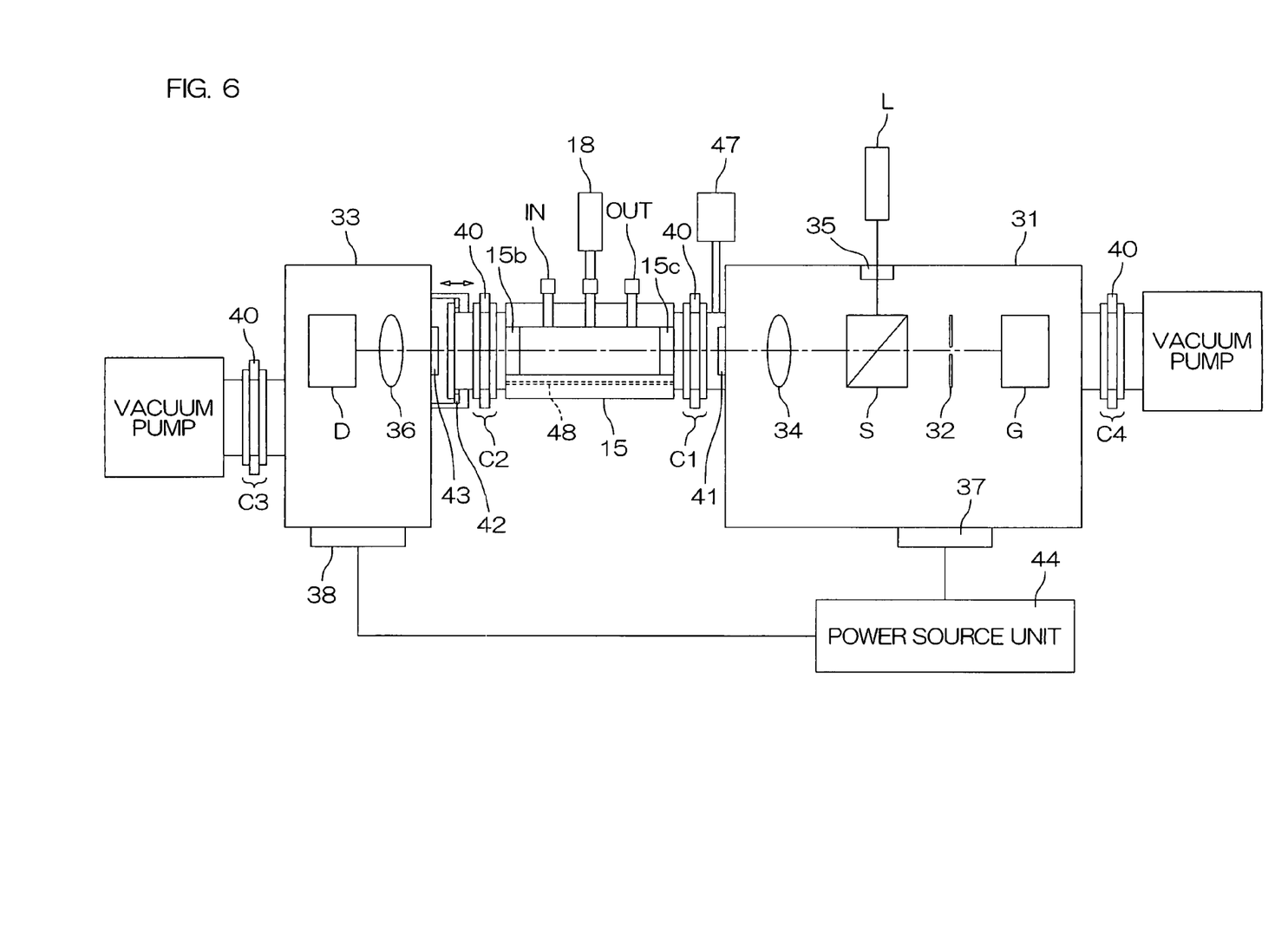
FIG. 6 is a view illustrating a measuring system in which an infrared source G, an interferometer S, an infrared detector D and the like are disposed inside of highly airtight containers.

FIG. 6 is a view illustrating a measuring system in which the infrared source G, the interferometer S, the infrared detector D and the like are disposed inside of a highly airtight container.

In FIG. 6, the gas flow passages such as the gas introducing system and the like are omitted. The infrared source G and the interferometer S are disposed inside of a highly airtight container 31 together with a slit 32 and a focusing lens or mirror 34 in the optical path. A vacuum connector 37 is disposed at the outer wall of the bottom of the highly airtight container 31. A power supply cable from a power source unit 44, and the like are connected to the vacuum connector 37. A vacuum pump inlet port is connected to a joint C4.

Laser light from a laser device L is introduced into the highly airtight container 31 through a light transmitting window 35. In the interferometer S, this laser light is used for selecting light having a specific wavelength. It is noted that the structure of the interferometer S using the laser device L, can be applied to the arrangement in FIG. 1.

A joint C1 for connection to the gas cell 15 is attached to a lateral wall of the highly airtight container 31. A light transmitting window 41 is mounted on the joint C1. The joining portion between the joint C1 and the light transmitting window 41 is maintained in airtightness. Accordingly, no gas leaks from the joint C1 to maintain the airtightness inside of the highly airtight container 31. An O-ring 40 is disposed for connecting the joint C1 to the gas cell 15.

Further disposed is a highly airtight container 33 which houses the infrared detector D. A focusing lens or mirror 36 is housed in the highly airtight container 33 together with the infrared detector D. A vacuum connector 38 is disposed at the outer wall of the bottom of the highly airtight container 33. A power supply cable from the power source unit 44, and the like, are connected to the vacuum connector 38. A vacuum pump inlet port is connected to a joint C3.

A joint C2 for connection to the gas cell 15 is disposed also at a lateral wall of the highly airtight container 33. A light transmitting window 43 is mounted on the joint C2. The joint C2 has an O-ring 40, through which the highly airtight container 33 is connected to the gas cell 15. The joint C2 is movable in the optical axis direction for facilitating the attachment and removal of the container 33 to and from the gas cell 15. An O-ring 42 is disposed to prevent the gas from leaking when the joint C2 is moved in the optical axis direction.

Further, a vacuum pump can be connected to a connector 47 of the joint C1 for removing both air which has entered the space between the window 41 of the joint C1 and the window 15c of the gas cell 15, and air which has entered the space between the window 15b of the gas cell 15 and the window 43 of the joint C2. These two spaces communicate with each other through a through-hole 48 formed in the gas cell 15. Accordingly, the airs inside of the two spaces can simultaneously be sucked merely by connecting the vacuum pump to the connector 47 of the joint C1.

According to the embodiment of the present invention, provision is made such that other main component elements such as the laser device L, the power source unit 44 and the personal computer and the like, than the infrared source G, the interferometer S and the infrared detector D, are disposed outside of the highly airtight containers 31, 33. That is, a heat convection current is extremely reduced in a vacuum. Accordingly, if these laser device, power source unit, computer and the like are disposed inside of the highly airtight containers 31,33, heat from these laser device, power source unit, computer and the like, is not transferred to the outside. This abnormally increases the temperatures inside of the highly airtight containers 31, 33 to exert a bad influence upon the measuring systems.

In the measuring system shown in FIG. 6, when the absorbance spectrum of the impurity gas is measured according to the method discussed in connection to FIGS. 1 to 5 with the highly airtight containers 31, 33 evacuated to lower the atmospheric pressure therein (e.g., 10$^{-4}$ to 10$^{-6}$ Torr), this eliminates the influence exerted by those components present in the air which absorb infrared rays. Accordingly, a more precise absorbance measurement can be conducted.

Figure 7:
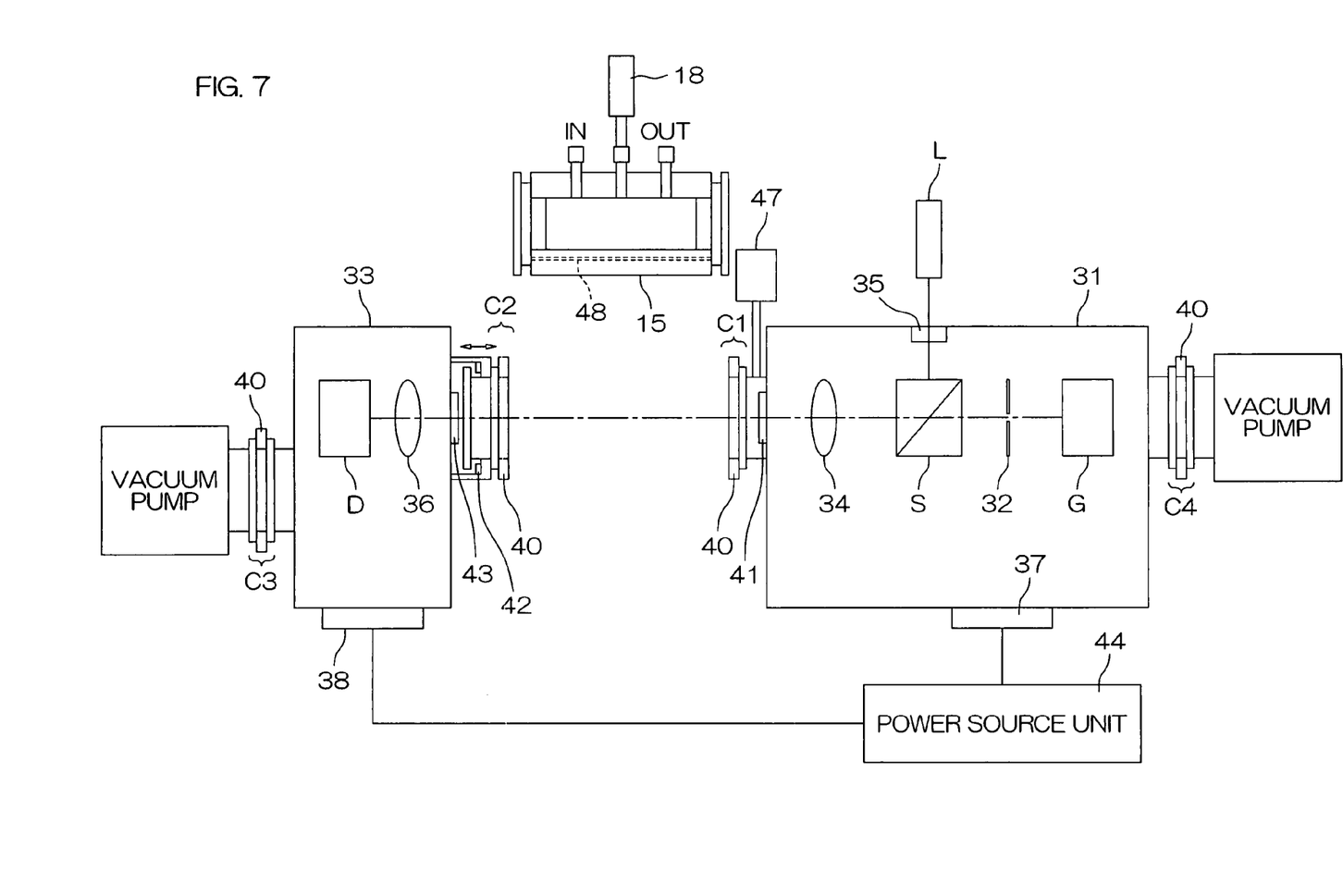
FIG. 7 is a view illustrating the measuring system in FIG. 6 with the gas cell 15 removed as disconnected from the joint C2.

FIG. 7 is a view illustrating the measuring system in FIG. 6 with the gas cell 15 removed as disconnected from the joint C2. According to this arrangement, the gas cell 15 can be replaced with other gas cell. As mentioned earlier, the joints C1, C2 maintain the airtightness of the highly airtight containers 31, 33. Accordingly, even at the time of gas cell replacement, the vacuum degree of each of the highly airtight containers 31, 33 is not lowered. Accordingly, upon completion of the replacement, measurement can immediately be started.

In the foregoing, embodiments of the present invention have been discussed. However, the present invention should not be limited to the embodiments above-mentioned. For example, a longer wavelength (40 μm) than that discussed in the foregoing, may be used. In this case, there can be measured a component which could not conventionally be measured, and or a component for which measurement was conventionally difficult (e.g., a tungsten compound or a phosphorus compound). In this case, however, it is required that each of the light transmitting windows 15b, 15c of the gas cell, the light transmitting windows 41, 43 of the joints C1, C2, and the light transmitting portion of the interferometer S, is made of a material capable of transmitting light in such a longer wavelength. For example, when the light transmitting portion of the interferometer S is made of CsI (cesium iodide), and the light transmitting windows are made of KRS-5 (thallium bromide 45.7%+thallium iodide 54.3%), a stable measurement can be conducted in an infrared range (The CsI is an optical material having a light transmitting rate of 80% or more in the wavelength range from 0.5 to 40 μm, and the KRS-5 is an optical material having a light transmitting rate of 70% or more in the wavelength range from 3 to 40 μm).

Further, the window 41 of the joint C1 and the window 43 of the joint C2 may be removed. According to this arrangement, the airtightness in each of the highly airtight containers 31, 33 can be maintained by connecting the gas cell 15 to the joints C1, C2. The two highly airtight containers 31, 33 communicate with each other through the through-hole 48 of the gas cell 15. Accordingly, the highly airtight containers 31, 33 can be evacuated in their entirety merely by connecting a vacuum pump to one of the containers 31, 33.

The disclosure of Japanese patent application serial No. 2004-210693, filed on Jul. 16, 2004, is incorporated herein by reference.

We claim:

1. A method of determining the concentration of impurity mixed in gas, comprising the steps of:
    (a) removing impurity from gas, introducing the gas into a first cell, and measuring the intensity of light transmitted through the first cell;
    (b) introducing gas containing impurity of which concentration is known, into the first cell or a second cell having an optical path length equal to that of the first cell, and measuring the intensity of light transmitted through the first cell or the second cell with the temperature and pressure maintained at those used at the measurement (a) above-mentioned;
    (c) dividing the light intensity obtained at the measurement (b) above-mentioned by the light intensity obtained at the measurement (a) above-mentioned, thereby to obtain the absorbance of the impurity, and storing this impurity absorbance in terms of a function of an impurity concentration;
    (d) introducing gas containing impurity of which concentration is unknown, into the first cell, the second cell or a third cell having an optical path length equal to that of the first cell, and measuring the intensity of light transmitted through the first cell, the second cell or the third cell with the temperature and pressure maintained at those used at the measurement (a) above-mentioned; and
    (e) dividing the light intensity obtained at the measurement (d) above-mentioned by the light intensity obtained at the measurement (a) above-mentioned, thereby to obtain the absorbance of the impurity, and applying the absorbance thus obtained to the function, thereby to obtain the impurity concentration.

2. Apparatus for determining the concentration of impurity mixed in gas, comprising:
    a cell into which gas is introduced;
    a light source for irradiating light to the cell;
    a detector for measuring the intensity of light transmitted through the cell;
    heat-insulating means for maintaining the cell at a fixed temperature;
    pressure adjusting means for adjusting the pressure of the gas in the cell to a predetermined value;
    a first gas introducing system for introducing, into the cell, a sample gas of which impurity concentration is to be measured;
    a second gas introducing system for introducing, into the cell, gas containing impurity of which concentration is known;
    an impurity removing device disposed in the first gas introducing system for removing impurity from a sample gas;
    first light intensity measuring means for introducing, into the cell, gas of which impurity has been removed by the impurity removing device, and for measuring the intensity of light transmitted through the cell;
    second light intensity measuring means for introducing, into the cell, gas containing impurity of which concentration is known, and for measuring the intensity of light transmitted through the cell;
    storing means for dividing the light intensity obtained by the measurement conducted with the second light intensity measuring means, by the light intensity obtained by the measurement conducted with the first light intensity measuring means, thereby to obtain the absorbance of the impurity, and for storing the impurity absorbance thus obtained in terms of a function of an impurity concentration;
    third light intensity measuring means for introducing, into the cell, gas containing impurity of which concentration is unknown, and for measuring the intensity of light transmitted through the cell; and
    concentration measuring means for dividing the light intensity obtained by the measurement conducted with the third light intensity measuring means, by the light intensity obtained by the measurement conducted with the first light intensity measuring means, thereby to obtain the absorbance of the impurity, and for applying the thus obtained impurity absorbance to the function stored in the storing means, thereby to obtain the impurity concentration.

3. Apparatus for determining the concentration of impurity mixed in gas according to claim 2, wherein the measurements are conducted with the light source housed in a first airtight container and with the detector housed in a second airtight container.

4. Apparatus for determining the concentration of impurity mixed in gas according to claim 3, wherein
    the joint portion between the first airtight container and the cell is capable of maintaining the airtightness in the first airtight container with the cell removed, and
    the joint portion between the second airtight container and the cell is capable of maintaining the airtightness in the second airtight container with the cell removed.

5. Apparatus for determining the concentration of impurity mixed in gas according to claim 3, wherein a power source unit for supplying an electric power to the light source or the detector, is disposed outside of the first and second airtight containers.

6. Apparatus for determining the concentration of impurity mixed in gas according to claim 3,
further comprising a computer for achieving the function of each of the first light intensity measuring means, the second light intensity measuring means, the storing means, the third light intensity measuring means and the concentration measuring means,
the computer being disposed outside of the first and second airtight containers.

* * * * *